(12) United States Patent
Smith et al.

(10) Patent No.: US 7,104,401 B2
(45) Date of Patent: Sep. 12, 2006

(54) PACKAGING ASSEMBLY FOR SURGICAL INSTRUMENTS

(75) Inventors: Daniel J. Smith, Dayton, NJ (US);
Joseph A. Pergine, Chalfont, PA (US)

(73) Assignee: Ethicon, Inc., Somerville, NJ (US)

( * ) Notice: Subject to any disclaimer, the term of this patent is extended or adjusted under 35 U.S.C. 154(b) by 428 days.

(21) Appl. No.: 10/706,734

(22) Filed: Nov. 12, 2003

(65) Prior Publication Data

US 2005/0098460 A1    May 12, 2005

(51) Int. Cl.
  *A61B 19/02*  (2006.01)
(52) U.S. Cl. .................. 206/366; 206/366; 206/438; 206/459.5; 600/29
(58) Field of Classification Search ............. 206/363, 206/364, 365, 366, 370, 438, 564, 570, 571, 206/459.5; 600/29, 151
See application file for complete search history.

(56) References Cited

U.S. PATENT DOCUMENTS

| | | | | |
|---|---|---|---|---|
| 5,405,005 | A | * | 4/1995 | White ..................... 206/363 |
| 6,394,269 | B1 | * | 5/2002 | Rudnick et al. ............ 206/380 |
| 6,814,236 | B1 | * | 11/2004 | Roshdy ..................... 206/570 |
| 6,911,003 | B1 | * | 6/2005 | Anderson et al. ........... 600/30 |
| 2003/0130670 | A1 | | 7/2003 | Anderson et al. |
| 2003/0171644 | A1 | | 9/2003 | Anderson et al. |
| 2005/0077197 | A1 | * | 4/2005 | Detruit et al. ............. 206/363 |
| 2005/0085834 | A1 | * | 4/2005 | Carranza et al. ............ 606/153 |

FOREIGN PATENT DOCUMENTS

EP   0 470 308 A1   2/1992

OTHER PUBLICATIONS

International Search Report dated Apr. 1, 2005, for corresponding international application No. PCT/US2004/036700.
U.S. Appl. No. 10/699,045, filed Oct. 31, 2003.
U.S. Appl. No. 10/706,559, filed Nov. 12, 2003.

* cited by examiner

*Primary Examiner*—David T. Fidei

(57) ABSTRACT

A packaging assembly for packaging a surgical device including first and second needle assemblies at least a distal portion of which having a curved configuration including an inner package member having first and second recesses sized and shaped for receiving at least a handle portion of the first and second needle assemblies. The recesses extend inwardly from the distal end of the inner package member a distance so that the distal curved portions of the needle assemblies extend beyond the distal end of the inner package. The distal end has a height such that the curved distal portions do not contact a surface on which the inner package member rests. The assembly further includes an outer package member dimensioned to removably receive therein the inner package member and the surgical device. The outer package member has a height sufficient so that when the inner package member and surgical devices are received therein, the outer package element remains substantially clear from contact with the surgical devices. The inner package member and surgical device can be removed from the outer package member and placed on a substantially flat surface in a manner such that the surgical device retains its orientation, and the distal portions of the needle assemblies remain clear of the surface.

17 Claims, 4 Drawing Sheets

PACKAGING ASSEMBLY FOR SURGICAL INSTRUMENTS

BACKGROUND OF THE INVENTION

1. Field of the Invention

The present invention relates generally to packaging for surgical devices, with particular application for packaging a surgical device for placing a suburethral sling to treat urinary incontinence.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle and shy away from social situations.

One device and method for placing a sub-urethral sling is described in detail in U.S. Pat. No. 5,899,909. This patent discloses a surgical instrument comprising a shank having a handle at one end and connecting means at the other end to receive, one at a time, two curved needle-like elements which are connected at one end to one end of a mesh intended to be implanted into the body. In practice, the mesh is passed into the body via the vagina first at one end and then at the other end, at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. This trans-vaginal procedure is exemplified by the TVT product sold by the Gynecare franchise of Ethicon Inc., a Johnson & Johnson Company, of Somerville, N.J., USA. In this procedure two 5 mm needles pass a PROLENE mesh trans-vaginally and through the abdomen to create a tension-free support around the mid urethra.

Sub-urethral slings have also been place by a different approach, wherein a needle is passed first though the abdominal wall, along the same path as described above, and eventually exiting through the vaginal incision. The tape is then coupled to the needle in some manner, and pulled back through the body from the vaginal incision and out through the abdominal incision. The chosen approach, vaginal or abdominal, will often depend on the preferences of the surgeon.

Yet another approach for implanting a sub-urethral sling has also been recently developed. In a "transobturator" approach, the implanted sling extends from beneath the urethra, and out through the obturator hole on either side. The procedure may involve inserting an appropriately configured needle from a vaginal incision and subsequently out through the obturator hole, or vice versa. The former technique (an "inside-out" approach) has been performed using a surgical instrument substantially similar to that shown in FIG. 1. This instrument is described in greater detail in copending U.S. patent application Ser. No. 10/699,045, which was filed on Oct. 31, 2003 and entitled "Guide for Surgical Device for the Treatment of Urinary Incontinence", and Ser. No. 10/706,559, which was filed on Nov. 12, 2003 and entitled "Improved Surgical Instrument and Method for the Treatment of Urinary Incontinence," which are incorporated herein by reference in their entirety. The surgical instrument or assembly 100 includes two needle assemblies 114, 116 that include two surgical passers 101, 103 that are secured at proximal ends to handles 102, 104. The surgical passers are curved and form a somewhat helical shape, and are mirror images of one another so that one 101 is particularly suited for passage through the body on the left side of the urethra, whereas the other 103 is particularly suited for passage on the opposite (right) side of the urethra. The needle assembly further includes tube elements 106, 108 that are removably applied over the ends of the surgical passers. Proximal ends of the tube elements are coupled to the tape 110 to be implanted as a sling beneath the urethra. The tape is preferably of knitted mesh construction, such as Prolene® polypropylene mesh (manufactured by Ethicon, Inc. of Somerville, N.J.) having dimensions of approximately ½×18 inches. The tape is also preferably covered by a plastic sheath that overlaps in the middle section so as to be easily removably. The surgical assembly may also include a guide element 112 to help guide the needle assemblies through the patient's body and to ensure safe passage thereof.

To implant a sub-urethral tape using the surgical assembly described above, the patient is first placed in the dorsal lithotomy position with the hips hyperflexed over the abdomen, and the bladder emptied. Next, the exit points of the surgical needles through the obturator foramen are marked. A midline incision is then made in the vaginal mucosa, and the left and right sides dissected with scissors or the like until it reaches and dissects the obturator membrane. The guide element 112 is then inserted through the vaginal incision and into the dissected tract until is passes the inferior pubic ramus and enters the opening previously made in the obturator membrane.

Once the guide element is fully inserted on one side as described above, the surgical passer 101 with associated tube element 106 (the needle assembly) for that side of the body is then inserted. The assembly is positioned within the guide member and passed through the dissected tract following the channel of the guide element from the vaginal incision and through the obturator membrane. Once the tip of the assembly traverses the obturator membrane, the guide element is removed. The assembly is rotated the remainder of the way through until the tip emerges from the skin at the exit point. The end of the tube element is then grasped, and the surgical passer reverse rotated to bring it back through the dissected tract and out through the vaginal incision. Subsequently, the tube element is pulled through the skin incision until the tape 110 exits the skin incision. The process is then repeated on the patient's other side and the tape adjusted, leaving the tape to form the sub-urethral sling beneath the mid-portion of the urethra.

When it comes to packaging the surgical assembly described above, several challenges have been encountered.

First, the needle assemblies are each designed for passing the tape through one specific side of the body and on one side of the urethra. Further, they are specifically designed for passing the tape from the vaginal incision and out through the obturator foramen, or an "inside-out" approach. In other words, a given needle is designed for use on one side of the body in one direction, such that a needle for use in passing the tape on the left side would be different depending on whether using an "inside-out" or "outside-in" approach. Thus, it is important that during transition from the packaging during surgery, there is limited room for opportunity for mixing up the needles. The transition and presentation should best ensure limited entanglement of the tape, and that all elements remain sterile. An additional concern is for the guide element, as it is used prior to inserting the first needle, and then again prior to inserting the second needle. A convenient way must be available to ensure sterility between uses.

Another packaging concern is ensuring that the tube elements, which are assembled over curved helical needles of opposing pitches, are not jostled relative to the needle, which would require re-assembly prior to use. Yet another packaging concern is ensuring that the sheath and mesh assembly is not kinked or damaged during storage or transit, as damage thereto could render the device inoperative. Further, it is important that the packaging and other device elements not be damaged by the sharp tip of the tube elements, and that the sharp tip itself not be damaged. The packaging according to the present invention overcomes these challenges, as well as provides a means by which to cleanly and efficiently present the surgeon with the instruments needed for performing the surgical procedure.

SUMMARY OF THE INVENTION

The present invention provides a packaging assembly for packaging a surgical device including first and second needle assemblies at least a distal portion of which having a curved configuration. The assembly includes an inner package member having a proximal end, a distal end, an upper side, a lower side, and first and second recesses therein sized and shaped for receiving therein at least a handle portion of said first and second needle assemblies. The first and second recesses extend inwardly from the distal end along the upper side a distance such that when the first and second needle assemblies are received therein, the distal curved portion thereof extends beyond the distal end of the inner package, and the distal end has a height such that when the first and second needle assemblies are received therein, the curved distal portions thereof do not contact a surface on which the lower side of the inner package member rests. The assembly further includes an outer package member having a proximal end, a distal end and a lower inner side, and dimensioned to removably receive therein the inner package member and the surgical device so that the lower side of the inner package member rests on the lower inner side of the outer package member. The outer package has a height sufficient so that when the inner package member and surgical devices are received therein, the outer package element remains substantially clear from contact with the surgical devices. The inner package member and surgical device can be removed from the outer package member and placed so that the lower side of the inner package member rests on a substantially flat surface, and when so removed the surgical device retains its orientation, and the distal portions of the needle assemblies remain clear of said surface.

According to one embodiment, the surgical device further includes a guide member, and the inner package member further includes a third recess therein dimensioned to removably receive therein the guide member. In yet another embodiment, the first recess is positioned on a right side of the inner package member and the first needle assembly is designed for use on a patient's right side, and the second recess is positioned on a left side of said inner package member and the second needle assembly is designed for use on a patient's left side. In another embodiment, the inner package member further includes an illustration indicating which needle assembly is for use on which side of the patient's body.

In yet another embodiment, the height of the inner package member increases from the proximal end to the distal end.

In still another embodiment, the surgical device further includes a mesh to be implanted having a first end coupled to the first needle assembly and a second end coupled to the second needle assembly. The inner package member also further includes a groove extending laterally across the inner package member at a location proximal of the first and second recesses. The groove is dimensioned to receive therein a portion of the mesh such that when the surgical device is removably received within the inner package member, the mesh extends from the first needle assembly, along a first side of the package assembly, within the groove, along a second side of the package assembly, and to the second needle assembly to thereby retain its orientation.

In a further embodiment, the handle portions of the first and second needle assemblies are press fit within the first and second recesses, and in yet another embodiment, the outer package member has an open upper side. This open upper side may be sealable with Tyvek®, the Tyvek® being removable to thereby expose the inner package member and surgical device.

Also provided is a combination surgical assembly and packaging assembly including a surgical assembly for use in placing a urethral sling to treat urinary incontinence. The surgical assembly includes a first needle assembly for passing a first end of a sling through a patient's body on a first side of the patient's urethra, and a second needle assembly for passing a second end of the sling through the patients body on a second side of the patient's urethra. The first and second needle assemblies include a handle portion and an insertion assembly extending therefrom to a distal end. At least a distal portion of the insertion assembly has a curved configuration, and the sling has the first end coupled to the first needle assembly and the second end coupled to the second needle assembly. The combination further includes a packaging assembly including an inner package member removably receivable within an outer package member. The inner package member has a proximal end, a distal end, and first and second recesses therein extending inwardly from the distal end. The first and second recesses are dimensioned to removably receive therein at least a portion of the first and second needle assemblies, and have a length such that when the first and second needle assemblies are received therein, the curved distal portion thereof extends outwardly from the distal end of the inner package member. The inner package member further has a height at the distal end such that the curved distal portions of the first and second needle assemblies do not contact a surface on which the inner package member may rest. The outer package member is dimensioned to removably receive therein the inner package and surgical assembly such that the surgical assembly is clear of contact with the outer package member.

In another embodiment, the surgical assembly further includes a guide member, and the inner package member further includes a third recess therein dimensioned to removably receive therein the guide member. The guide member recess is positioned laterally across the inner package member at a location proximal of the first and second recesses.

In yet another embodiment, the inner package member further includes one or more finger grips for grasping to remove the inner package member from the outer package member, and in yet another embodiment, the height of the inner package member increases from the proximal end to the distal end.

In yet another embodiment, the inner package member further includes a groove extending laterally across the inner package member at a location proximal of the first and second recesses. The groove is dimensioned to receive therein a portion of the sling such that when the surgical assembly is removably received within the inner package member, the sling extends from the first needle assembly, along a first side of the package assembly, within the groove, along a second side of the package assembly, and to the second needle assembly to thereby retain its orientation.

The present invention further provides a package assembly for removably receiving therein a surgical assembly. The package assembly includes an inner package member removably receivable within an outer package member, the inner package member having first and second recesses therein extending inwardly from a distal end thereof. The first and second recesses are dimensioned to removably receive therein at least a portion of first and second surgical instruments designed specifically for use on first and second sides of a patient's body respectively. The first and second surgical instruments have a curved portion at a distal end that, when the first and second instruments are removably received within the first and second recesses, extends outwardly from the distal end of the inner package member. The inner package member has a height that increases from the proximal end to the distal end, the height being sufficient at said distal end such that when the inner package member is removed from the outer package member and placed on a substantially flat surface, the curved portions of the surgical instruments do not contact said surface.

In another embodiment, the inner package member further comprises a third recess therein dimensioned to removably receive therein a guide member. In yet another embodiment, the surgical assembly further includes a mesh to be implanted, a first end of which is coupled to the first surgical instrument and a second end of which is coupled to the second surgical instrument, and the inner package member further includes a groove extending laterally across the inner package member at a location proximal of the first and second recesses. The groove is dimensioned to receive therein a portion of the mesh such that when the surgical assembly is removably received within the inner package member, the mesh extends from the first surgical instrument, along a first side of the inner package member, within the groove, along a second side of the inner package member, and to the second surgical instrument to thereby retain its orientation.

These and other features and advantages of the present invention will become apparent from the following more detailed description, when taken in conjunction with the accompanying drawings which illustrate, by way of example, the principles of the invention.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways.

Figure 1:
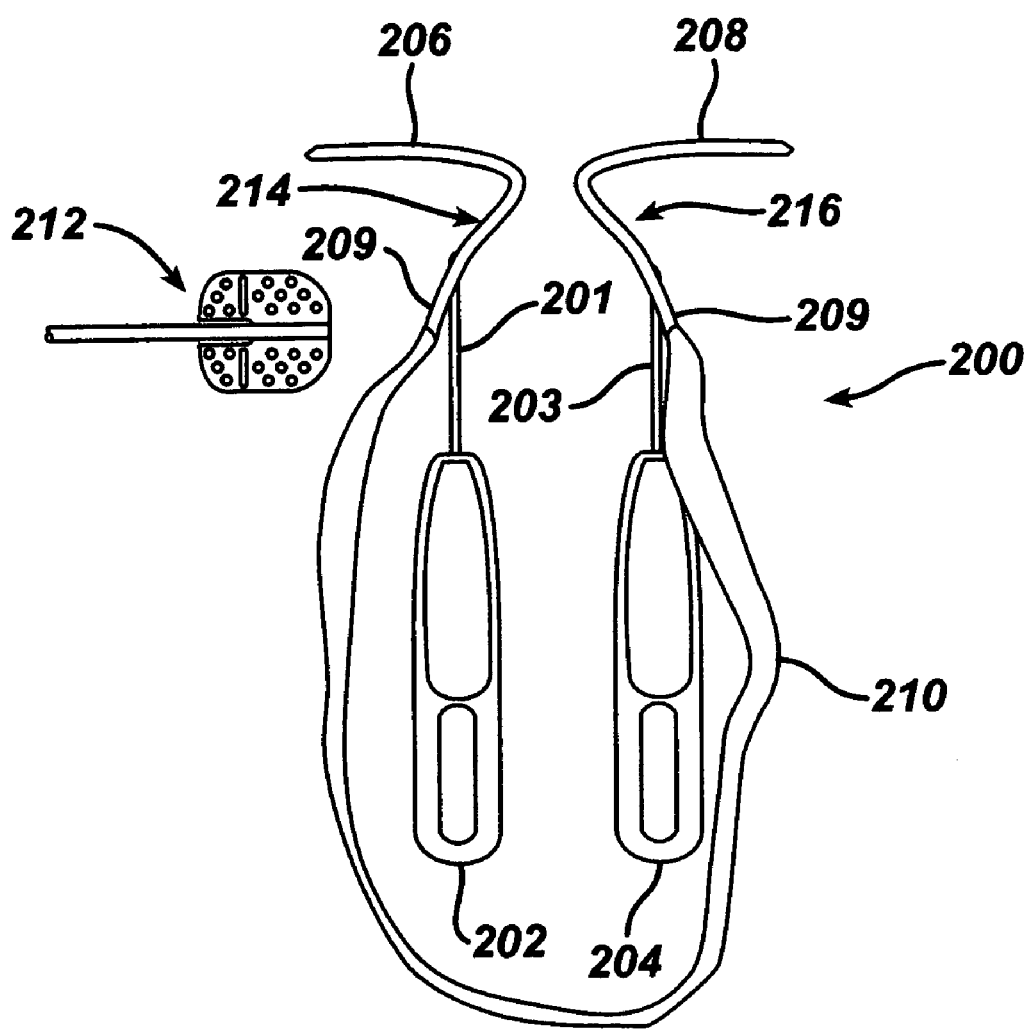
FIG. 1 illustrates exemplary surgical instruments to be carried by packaging assembly of the present invention.
Figure 2:
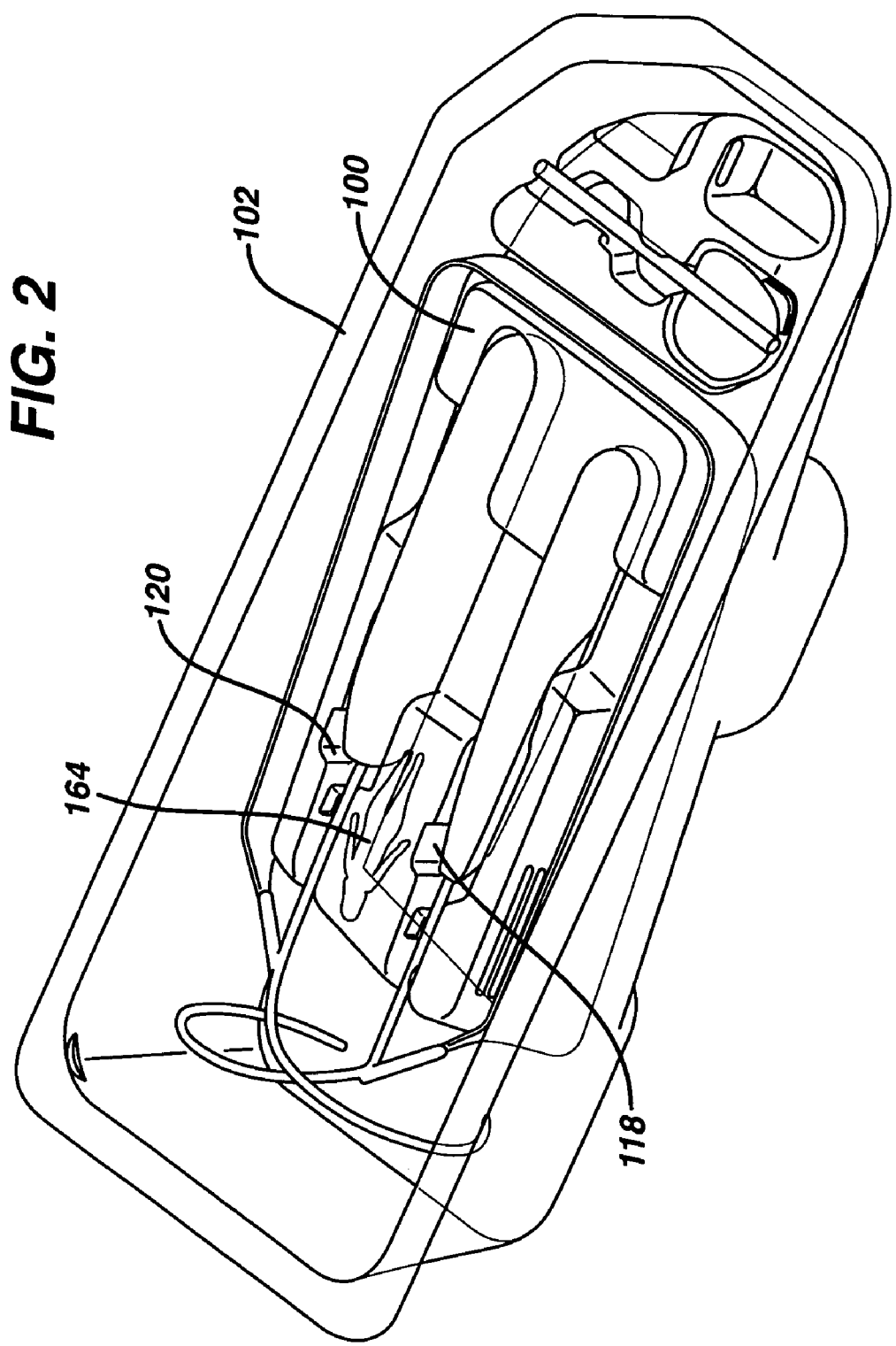
FIG. 2 is a perspective view of a packaging assembly according to the present invention.
Figure 3:
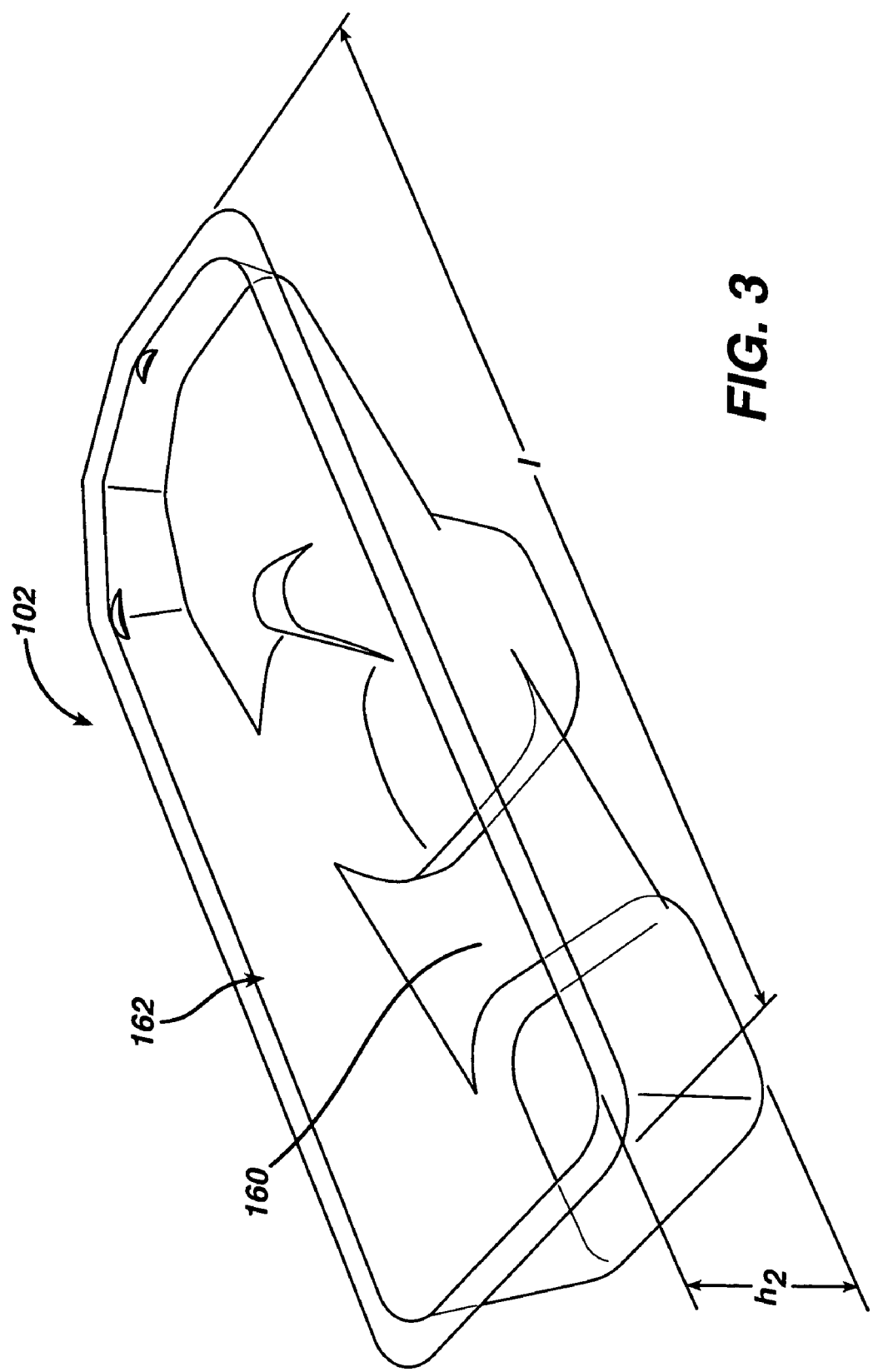
FIG. 3 is a perspective view of an outer package element of the packaging assembly of FIG. 2.
Figure 4:
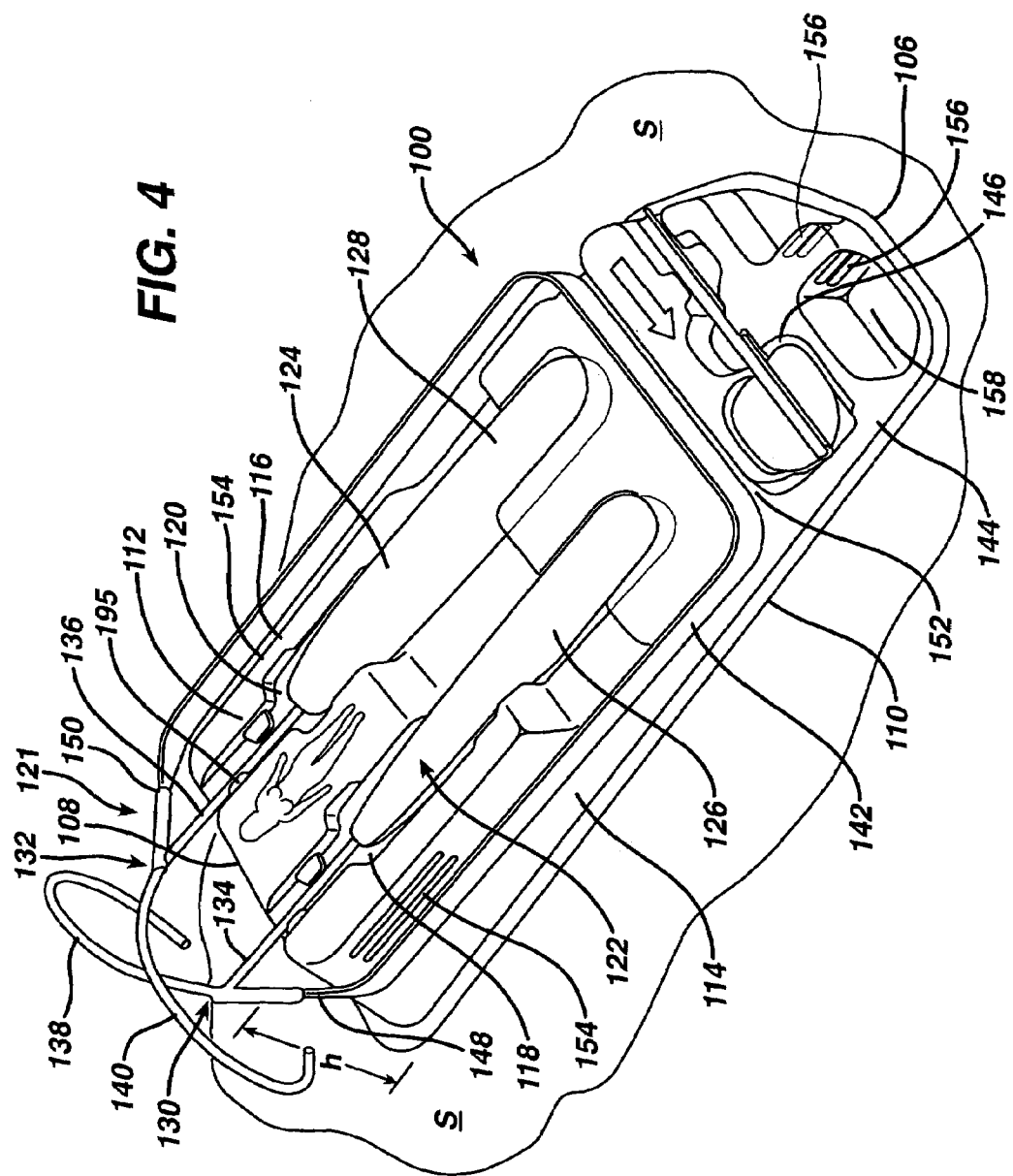
FIG. 4 is a perspective view of an inner package element of the packaging assembly of FIG. 2.

FIGS. 2–4 illustrate one embodiment of a package assembly according to the present invention. The package assembly includes an inner package member 100 (FIG. 4) and an outer package member 102 (FIG. 3), wherein the inner package member is removably receivable within the outer package member as shown in FIG. 2. The inner package member includes a proximal end 106, a distal end 108, a lower side 110 on which it rests, an upper side 112, and first 114 and second 116 sides. The inner package member also includes first and second recesses 118, 120 for receiving therein first and second surgical instruments 122, 124 such as the first and second surgical needle assemblies shown in FIG. 4. The surgical needle assemblies shown in FIG. 4 are those which are described above for use in a trans-obturator procedure to implant a sub-urethral sling. Although this specific type of surgical assembly is illustrated and described herein, it is to be understood that the package assembly according to the present invention can also be used with other suitable surgical assemblies or devices.

Referring once again to FIG. 4, the illustrated surgical assembly 121 includes first and second surgical instruments 122, 124 which are each needle assemblies having handle portions 126, 128 and insertion assemblies 130, 132 extending from the handle portions. By insertion assemblies it is meant simply that the insertion assemblies, or some portion thereof, are what it inserted into the patient's body. In the illustrated embodiment, the insertion assemblies include a wire element 134, 136 and a tube element 138, 140 inserted over a distal end of the wire element as described above. At least a distal portion of the insertion assemblies have a curved configuration such as that illustrated. Further, the surgical assembly also includes a sling 142, such as a mesh, to be implanted into the patient as is also described above.

The first and second recesses 118, 120 in the inner package member extend inwardly from a distal end 106 and along the upper side 112 of the inner package member. The first and second recesses are dimensioned to removably receive therein at least the handle portions 126, 128 of the first and second needle assemblies, but are further dimensioned relative to the needle assemblies, so that the curved distal portions of the needle assemblies extend outwardly beyond the distal end of the inner package member as shown. Preferably, the recesses are sized so that at least the handle portions can be snap-fit into the recesses. In one embodiment, appropriate spaces are formed around the recesses to facilitate grasping the handle portions for removal thereof. In another embodiment, the recesses further include tab elements 195 or the like that fit tighter to the instrument, than the remainder of the recess, and it is primarily these tab elements that cause the "snap-fit" between the instrument and the recess. The inner package member further has a height h at the distal end such that the curved distal portions of the needle assemblies do not contact the surface S on which the inner package member rests. Preferably, the height of the inner package member increases gradually from the proximal end 106 to the distal end 108. When the inner package member is removed from the outer package member and placed, for example, on a surgical table, this configuration presents the surgical assembly to the surgeon in a more ergonomic fashion.

The surgical assembly may also include a guide element 144, in which case the inner package member may also include a guide member recess 146 configured to be substantially complementary to the guide member to removably receive therein the guide member. Preferably, the guide member recess extends laterally across the inner package member at a location distal of the first and second recesses as shown. This enables the guide member to be presented to the surgeon independent of interference with removal of the first and/or second surgical instrument. This is important, in that the guide is used first and may be used more than once during a trans-obturator procedure.

As indicated above, the illustrated surgical assembly also includes a mesh 142 to be implanted into the patient. The mesh is coupled at a first end 148 to the first surgical instrument and at a second end 150 to the second surgical instrument. In providing a package for such a surgical assembly, it is also important to prevent the mesh from becoming twisted, or entangled with other components of the surgical instrument. The present packaging assembly achieves this objective by providing a groove 152 or the like that extends laterally across the inner package member at a location proximal of the first and second recesses (and distal of the guide member recess if one is present). This groove is positioned relative to the first and second recesses so that, when the surgical instruments are inserted therein, the mesh extents from the first surgical instrument, along the first side 114 of the inner package member, through the groove 152, along the second side 116 of the inner package member, and to the second surgical instrument as shown, thereby keeping the mesh properly oriented within the package and free from twisting or entanglement. The tapered space between the inner and outer packaging also allows the tangent portion of the needle tube to extend into this space without direct contact with the outer package wall, thus limiting damage to the sheath/mesh or its attachment.

The inner package member may also include one or more sets of finger grips 154, 156. The finger grips are preferably positioned on sides of the inner package member, or sides of a grip recess 158 or the like, so that a user can readily grasp the inner package member to remove it from the outer package member or otherwise pick it up without interfering with the surgical assembly.

Referring now to FIGS. 2 and 3, the package assembly also includes an outer package member 102 designed to removably receive therein the inner package member. The outer package member is dimensioned to receive therein the inner package member so that there is very little, if any, room for movement of the inner package member. It is also dimensioned so that there is substantially no interference or contact between the outer package member and the surgical assembly. In particular, the height h2 of the outer package member is sufficient to clear the curved distal portions of the surgical instruments that extend beyond the inner package member. Similarly, the length l of the outer package member must also be sufficient to clear the curved distal portions.

The outer package member also has a lower inner side 160 and an upper side 162. In the illustrated embodiment, the upper side 162 is open, but is covered by a Tyvek® wrap or the like (not shown). The package is sterilized using ethylene oxide gas, which will penetrate through the Tyvek® cover. Tyvek® material is widely known and used in the industry as a sterile barrier, once exposed to ethylene oxide gas and an upper seal to hold it in place relative to the package.

The above-described assembly would be presented at the surgical site in substantially the same configuration as shown in FIG. 2, with a Tyvek wrap across the top as described above (not shown). The surgical staff would remove the Tyvek wrap, then subsequently remove the inner package member from the outer package member and place it on the surgical table, preferably by using the provided finger grips. The remaining inner package element and surgical assembly, as shown in FIG. 4, retains the surgical assembly in its proper orientation, but also presents the surgical assembly in a convenient manner for use. The inner package can also be "dumped" onto the sterile field, if needed prior to properly positioning it on its lower side, once the Tyvek® has been removed. The surgical instrument for use on the right side of the body 124 is presented on the right side of the package, and the surgical instrument for use on the left side of the body 122 is presented on the left side of the package. In one embodiment, the package assembly may also include an illustration 164, such as an embossment of a lady, that further illustrates which instrument is for use on which side of the body. If the devices were prematurely removed from the packaging, the illustration and package could be used as a guide to determine the proper orientation of the instruments. The surgical assembly is also presented in a manner that does not require pre-assembly of any of the elements, keeps the elements in their proper orientation relative to one another, prevents tangling or damage to the mesh, and ensures no damage to the pointed distal tips of the surgical instruments.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A packaging assembly for packaging a surgical device including first and second needle assemblies at least a distal portion of which having a curved configuration, comprising:

an inner package member having a proximal end, a distal end, an upper side a lower side, and first and second recesses therein sized and shaped for receiving therein at least a handle portion of said first and second needle assemblies, said first and second recesses extending inwardly from said distal end along the upper side a distance such that when the first and second needle assemblies are received therein, the distal curved portion thereof extends beyond the distal end of the inner package, and the distal end having a height such that when the first and second needle assemblies are received therein, the curved distal portions thereof do not contact a surface on which the lower side of the inner package member rests;

an outer package member having a proximal end, a distal end and a lower inner side, and dimensioned to removably receive therein the inner package member and the surgical device so that the lower side of the inner package member rests on the lower inner side of the outer package member, and having a height sufficient so that when the inner package member and surgical devices are received therein, the outer package element remains substantially clear from contact with the surgical devices;

wherein the inner package member and surgical device can be removed from the outer package member and placed so that the lower side of the inner package member rests on a substantially flat surface, and when so removed the surgical device retains its orientation, and the distal portions of the needle assemblies remain clear of said surface.

2. The package assembly according to claim 1, wherein the surgical device further includes a guide member, and the inner package member further comprises a third recess therein dimensioned to removably receive therein the guide member.

3. The package assembly according to claim 1, wherein the first recess is positioned on a right side of said inner package member and wherein the first needle assembly is designed for use on a patient's right side, and wherein the second recess is positioned on a left side of said inner package member and wherein the second needle assembly is designed for use on a patient's left side.

4. The package assembly according to claim 3, wherein the inner package member further comprises an illustration indicating which needle assembly is for use on which side of the patient's body.

5. The package assembly according to claim 1, wherein the height of the inner package member increases from the proximal end to the distal end.

6. The package assembly according to claim 1, wherein the surgical device further comprises a mesh to be implanted having a first end coupled to the first needle assembly and a second end coupled to the second needle assembly, wherein the inner package member further comprises a groove extending laterally across the inner package member at a location proximal of the first and second recesses, the groove being dimensioned to receive therein a portion of the mesh such that when the surgical device is removably received within the inner package member, the mesh extends from the first needle assembly, along a first side of the package assembly, within the groove, along a second side of the package assembly, and to the second needle assembly to thereby retain its orientation.

7. The package assembly according to claim 1, wherein the handle portions of the first and second needle assemblies are press fit within the first and second recesses.

8. The package assembly according to claim 1, wherein the outer package member has an open upper side.

9. The package assembly according to claim 8, wherein the open upper side is sealable with film, the film being removable to thereby expose the inner package member and surgical device.

10. A combination surgical assembly and packaging assembly comprising:
a surgical assembly for use in placing a urethral sling to treat urinary incontinence, the surgical assembly including a first needle assembly for passing a first end of a sling through a patient's body on a first side of the patient's urethra, and a second needle assembly for passing a second end of the sling through the patients body on a second side of the patient's urethra, the first and second needle assemblies including a handle portion and an insertion assembly extending therefrom to a distal end, at least a distal portion of the insertion assembly having a curved configuration, and said sling having the first end coupled to the first needle assembly and the second end coupled to the second needle assembly, a packaging assembly including an inner package member removably receivable within an outer package member, the inner package member having a proximal end, a distal end, and having first and second recesses therein extending inwardly from the distal end, the first and second recesses being dimensioned to removably receive therein at least a portion of the first and second needle assemblies, and having a length such that when the first and second needle assemblies are received therein, the curved distal portion thereof extends outwardly from the distal end of the inner package member, the inner package member further having a height at the distal end such that the curved distal portions of the first and second needle assemblies do not contact a surface on which the inner package member may rest, the outer package member dimensioned to removably receive therein the inner package and surgical assembly such that the surgical assembly is clear of contact with the outer package member.

11. The combination according to claim 10, wherein the surgical assembly further comprises a guide member, and the inner package member further comprises a third recess therein dimensioned to removably receive therein the guide member, the guide member recess being positioned laterally across the inner package member at a location proximal of the first and second recesses.

12. The combination according to claim 10, wherein the inner package member further comprises one or more finger grips for grasping to remove the inner package member from the outer package member.

13. The combination according to claim 10, wherein the height of the inner package member increases from the proximal end to the distal end.

14. The package assembly according to claim 10, wherein the inner package member further comprises a groove extending laterally across the inner package member at a location proximal of the first and second recesses, the groove being dimensioned to receive therein a portion of the sling such that when the surgical assembly is removably received within the inner package member, the sling extends from the first needle assembly, along a first side of the package assembly, within the groove, along a second side of the package assembly, and to the second needle assembly to thereby retain its orientation.

15. A package assembly for removably receiving therein a surgical assembly, the package assembly comprising:
an inner package member removably receivable within an outer package member, the inner package member having first and second recesses therein extending inwardly from a distal end thereof, the first and second recesses being dimensioned to removably receive therein at least a portion of first and second surgical instruments designed specifically for use on first and second sides of a patient's body respectively, the first and second surgical instruments having a curved portion at a distal end that, when the first and second instruments are removably received within the first and second recesses, extends outwardly from the distal end of the inner package member, the inner package member having a height that increases from the proximal end to the distal end, said height being sufficient at said distal end such that when the inner package member is removed from the outer package member and placed on a substantially flat surface, the curved portions of the surgical instruments do not contact said surface.

16. The combination according to claim 15, wherein the surgical assembly further comprises a guide member, and the inner package member further comprises a third recess therein dimensioned to removably receive therein the guide member.

17. The package assembly according to claim 15, wherein the surgical assembly further includes a mesh to be implanted, a first end of which is coupled to the first surgical instrument and a second end of which is coupled to the second surgical instrument, and wherein the inner package member further comprises a groove extending laterally across the inner package member at a location proximal of the first and second recesses, the groove being dimensioned to receive therein a portion of the mesh such that when the surgical assembly is removably received within the inner package member, the mesh extends from the first surgical instrument, along a first side of the inner package member, within the groove, along a second side of the inner package member, and to the second surgical instrument to thereby retain its orientation.

* * * * *